United States Patent
Coates et al.

(10) Patent No.: US 7,264,621 B2
(45) Date of Patent: Sep. 4, 2007

(54) MULTI-AXIAL BONE ATTACHMENT ASSEMBLY

(75) Inventors: Bradley J. Coates, Rossville, TN (US); Robert A. Farris, Cordova, TN (US); Harold Sparr Taylor, Memphis, TN (US); Jeffrey Wade Poyner, Bartlett, TN (US)

(73) Assignee: SDGI Holdings, Inc., Wilminton, DE (US)

( * ) Notice: Subject to any disclaimer, the term of this patent is extended or adjusted under 35 U.S.C. 154(b) by 387 days.

(21) Appl. No.: 10/870,011

(22) Filed: Jun. 17, 2004

(65) Prior Publication Data

US 2005/0283157 A1    Dec. 22, 2005

(51) Int. Cl.
*A61B 17/70* (2006.01)

(52) U.S. Cl. .......................................... 606/73; 606/61

(58) Field of Classification Search ................ 606/53, 606/60–61, 72–73, 78; 403/56, 76, 90, 112–144; 623/17.17
See application file for complete search history.

(56) References Cited

U.S. PATENT DOCUMENTS

| | | | |
|---|---|---|---|
| 4,763,644 A | 8/1988 | Webb | |
| 4,805,602 A | 2/1989 | Puno | |
| 5,207,678 A | 5/1993 | Harms et al. | |
| 5,217,497 A | 6/1993 | Mehdian | |
| 5,360,431 A | 11/1994 | Puno et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,501,684 A | 3/1996 | Schlapfer et al. | |
| 5,549,608 A | 8/1996 | Errico et al. | |
| 5,554,157 A | 9/1996 | Errico et al. | |
| 5,554,194 A * | 9/1996 | Sanders | 623/17.17 |
| 5,562,661 A | 10/1996 | Yoshimi et al. | |
| 5,575,792 A | 11/1996 | Errico et al. | |
| 5,586,984 A | 12/1996 | Errico et al. | |
| 5,609,593 A * | 3/1997 | Errico et al. | 606/61 |
| 5,672,176 A | 9/1997 | Biedermann et al. | |
| 5,690,630 A | 11/1997 | Errico et al. | |
| 5,716,356 A | 2/1998 | Biedermann et al. | |
| 5,728,098 A * | 3/1998 | Sherman et al. | 606/61 |
| 5,733,286 A | 3/1998 | Errico et al. | |
| 5,817,094 A | 10/1998 | Errico et al. | |

(Continued)

FOREIGN PATENT DOCUMENTS

WO    WO/2005/018471 A1    3/2005

*Primary Examiner*—Eduardo C. Robert
*Assistant Examiner*—Anitza M San Miguel
(74) *Attorney, Agent, or Firm*—Coats & Bennett, P.L.L.C.

(57) ABSTRACT

A posterior fixation system includes a saddle member and an anchoring member. The anchoring member anchors the saddle member to bone. The saddle member includes a pair of upright portions that define a channel. The saddle member further has a hole therethrough bounded by an inner wall, and the hole forms a lower opening in the saddle member. The lower opening in the saddle member may contain angular cutouts placed symmetrically about the axis of the saddle to increase the allowable angulation of the bone screw in relationship to the axis of the saddle. The channel is adapted to receive an orthopedic rod, and the hole in the saddle member is adapted to receive the anchoring member. The saddle member and the anchoring member can be coupled so as to allow multi-axial movement of the members.

39 Claims, 18 Drawing Sheets

U.S. PATENT DOCUMENTS

| | | | |
|---|---|---|---|
| 5,885,286 A | 3/1999 | Sherman et al. | |
| 5,891,145 A | 4/1999 | Morrison et al. | |
| 5,954,725 A | 9/1999 | Sherman et al. | |
| 5,961,517 A * | 10/1999 | Biedermann et al. | 606/61 |
| 6,010,503 A * | 1/2000 | Richelsoph et al. | 606/61 |
| 6,074,391 A | 6/2000 | Metz-Stavenhagen et al. | |
| 6,077,262 A | 6/2000 | Schlapfer et al. | |
| 6,090,111 A * | 7/2000 | Nichols | 606/61 |
| 6,132,432 A | 10/2000 | Richelsoph | |
| 6,132,434 A * | 10/2000 | Sherman et al. | 606/78 |
| 6,187,005 B1 | 2/2001 | Brace et al. | |
| 6,254,602 B1 * | 7/2001 | Justis | 606/61 |
| 6,280,442 B1 * | 8/2001 | Barker et al. | 606/60 |
| 6,296,642 B1 | 10/2001 | Morrison et al. | |
| 6,443,953 B1 | 9/2002 | Perra et al. | |
| 6,485,491 B1 | 11/2002 | Farris et al. | |
| 6,485,494 B1 * | 11/2002 | Haider | 606/73 |
| 6,520,963 B1 | 2/2003 | McKinley | |
| 6,540,748 B2 | 4/2003 | Lombardo | |
| 6,565,565 B1 * | 5/2003 | Yuan et al. | 606/61 |
| 6,652,526 B1 | 11/2003 | Arafiles | |
| 6,682,532 B2 | 1/2004 | Johnson et al. | |
| 7,022,122 B2 * | 4/2006 | Amrein et al. | 606/61 |
| 2002/0010467 A1 | 1/2002 | Cooper et al. | |
| 2002/0058942 A1 | 5/2002 | Biedermann et al. | |
| 2002/0151900 A1 | 10/2002 | Glascott | |
| 2003/0032957 A1 | 2/2003 | McKinley | |
| 2003/0167058 A1 | 9/2003 | Shluzas | |
| 2003/0216735 A1 | 11/2003 | Altarac et al. | |
| 2004/0181224 A1 | 9/2004 | Biedermann et al. | |
| 2004/0186473 A1 | 9/2004 | Cournoyer et al. | |

* cited by examiner

SECTION C-C

SECTION C-C

BOTTOM VIEW OF SADDLE

MULTI-AXIAL BONE ATTACHMENT ASSEMBLY

BACKGROUND OF THE INVENTION

The present invention generally relates to orthopedic implants used for correction of spinal injuries or deformities, and more specifically, but not exclusively, concerns apparatuses for fixing a portion of the spine, such as the cervical spine, to allow correction or healing thereof.

In the field of spinal surgery, it is known to place implants into vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Typical implant systems utilize a rod as the support and stabilizing member. In such an implant, a series of two or more screws are inserted into two or more vertebrae to be instrumented. A rod is then placed within or coupled to the heads of the screws, or is placed within a connecting device that links the rod and a screw head, and the connections are secured. In this way, a supporting structure is fixed to the vertebrae.

Many varieties of bone fixation screws are mono-axial in construction. That is, such devices are connected to the rod or plate such that a longitudinal axis through the rod or plate and a longitudinal axis through the fixation device are capable of only a single position with respect to each other. While useful in certain circumstances, in many therapeutic situations the degree of precision required to use such an inflexible device is impractical.

More recently, bone fixation devices having multi-axial capability have been introduced. Examples of such constructs are shown in U.S. Pat. Nos. 5,797,911, 5,954,725, 5,810,818 and 6,485,491 which is hereby incorporated by reference. These devices help to reduce the required precision of placement of the fixation device, since the saddle portion of the fixation device is multi-axially positionable on the anchor member portion. The saddle portion can thus be positioned so as to easily receive the rod, limiting or removing much of the positioning difficulty inherent in prior devices.

Most such devices are designed for spinal fixation at the thoracic and lumbar levels and allow only a limited angulation of the anchor member in relation to the saddle member. There is a need in the art for a multi-axial bone attachment assembly, and particularly one that is useful in the cervical region of the spine with a greater degree of such angulation.

SUMMARY OF THE INVENTION

One embodiment of the present invention is a unique multi-axial bone attachment assembly that includes a saddle member and a bone anchoring member. The saddle member has a plurality of upright portions that define a channel through the saddle member. The saddle member further has a hole therethrough bounded by an inner wall, and the hole forms a lower opening in the saddle member. The lower opening in the saddle member may contain angular cutouts placed symmetrically about the axis of the saddle to increase the allowable angulation of the bone screw in relationship to the axis of the saddle. The position, angle and number of cutouts may vary as required by the application of the multi-axial bone attachment assembly. The bone-anchoring member extends through the opening. The bone-anchoring member includes a head portion and an anchoring portion. A further embodiment of the present invention includes a washer (crown member). The washer may have a recessed portion for accommodating an orthopedic rod and may include a radially extending projection. The washer is fitted within the hole of the saddle member and atop the bone-anchoring member.

Further features and practical advantages of different embodiments of the invention will emerge from the description of the exemplified embodiments with reference to the figures.

DESCRIPTION OF THE PREFERRED EMBODIMENTS

Figure 1:
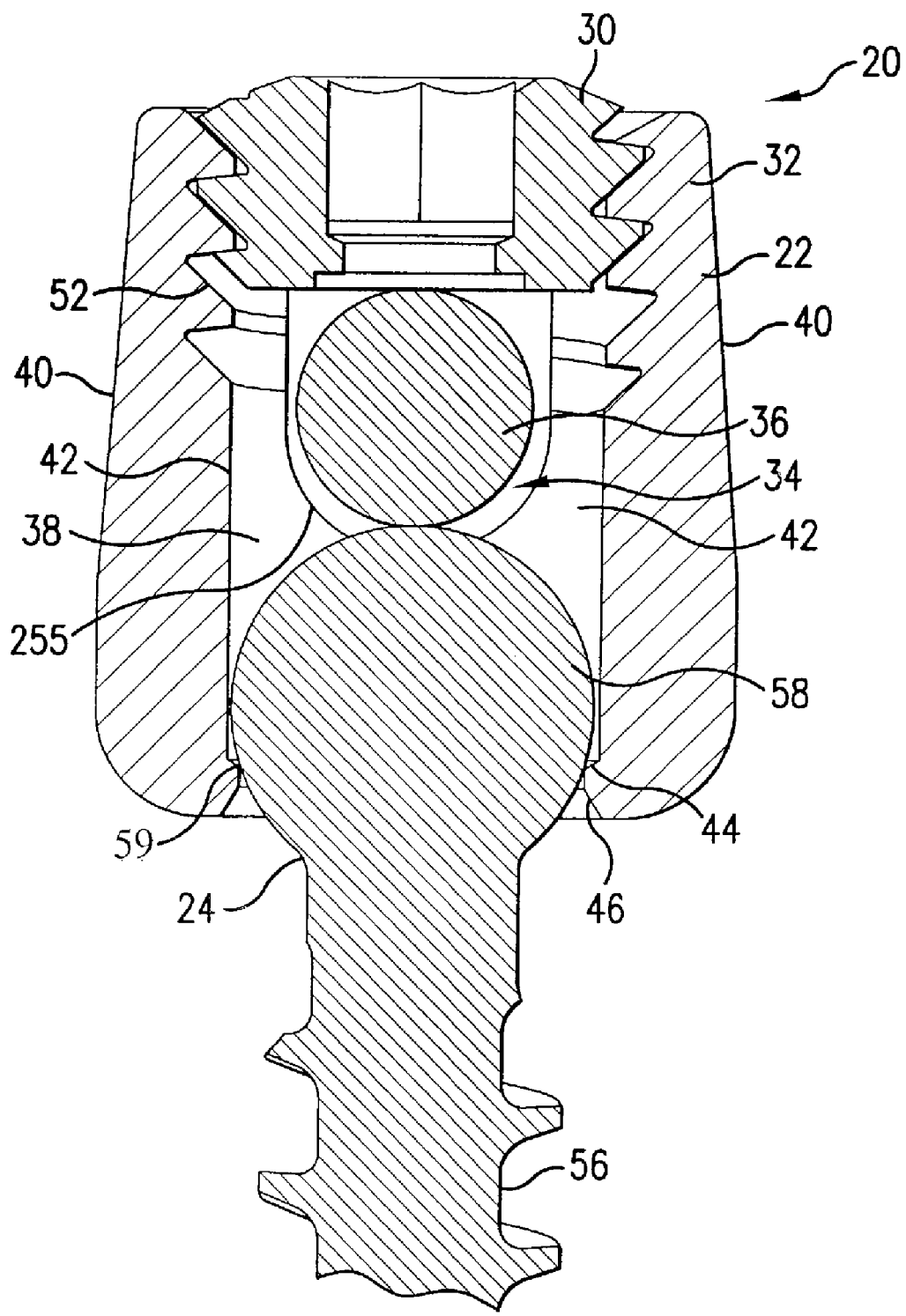
FIG. 1 shows a partial cross-sectional view of a bone anchor assembly according to one embodiment of the present invention.

Reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of embodiments of the invention as illustrated therein, being contemplated as would normally occur to one skilled in the art to which the invention relates.

Figure 3:
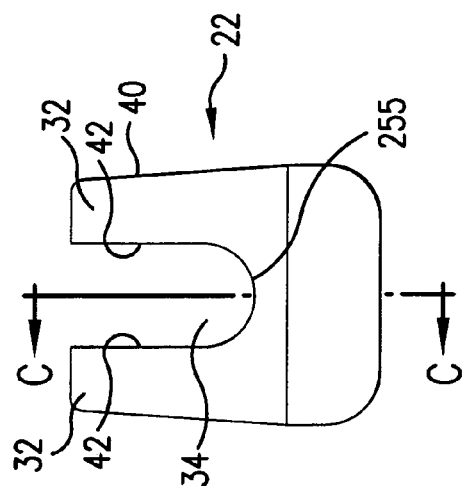
FIG. 3 shows a side view of a saddle member according to one embodiment of the present invention.

In FIG. 1, there is shown an embodiment of a multi-axial bone anchor assembly 20. Bone anchor assembly 20 includes a saddle member 22, a bone anchoring member 24, and set screw member 30. Saddle member 22 generally has a U-shape, with two upright portions 32 defining a channel 34 extending through saddle member 22. Channel 34 is then configured to accommodate an elongated member 36, such as a spinal rod. For posterior cervical fixation, rod 36 may have one of a number of desired lengths and diameters. As seen in FIG. 1, the width of channel 34 is slightly larger than the diameter of rod 36, which allows easier insertion of rod 36 into channel 34, also allows for compensation for contouring of the rod, and allows use of a range of rod sizes with the same saddle member 22. The curved bottoms 255, shown in FIG. 3, of channel 34 are arranged such that the top of the head portion 58 of the of bone anchor member 24, when fully nested into the lower portion of hole 38, extends above the edge of the curved bottoms 255 of channel 34 such that rod 36 positioned in channel 34 will pressingly engage the head portion 58 of bone anchor member 24. Saddle member 22 further includes a hole 38 therethrough, the axis of hole 38 being substantially perpendicular to the axis of channel 34.

Figure 2:
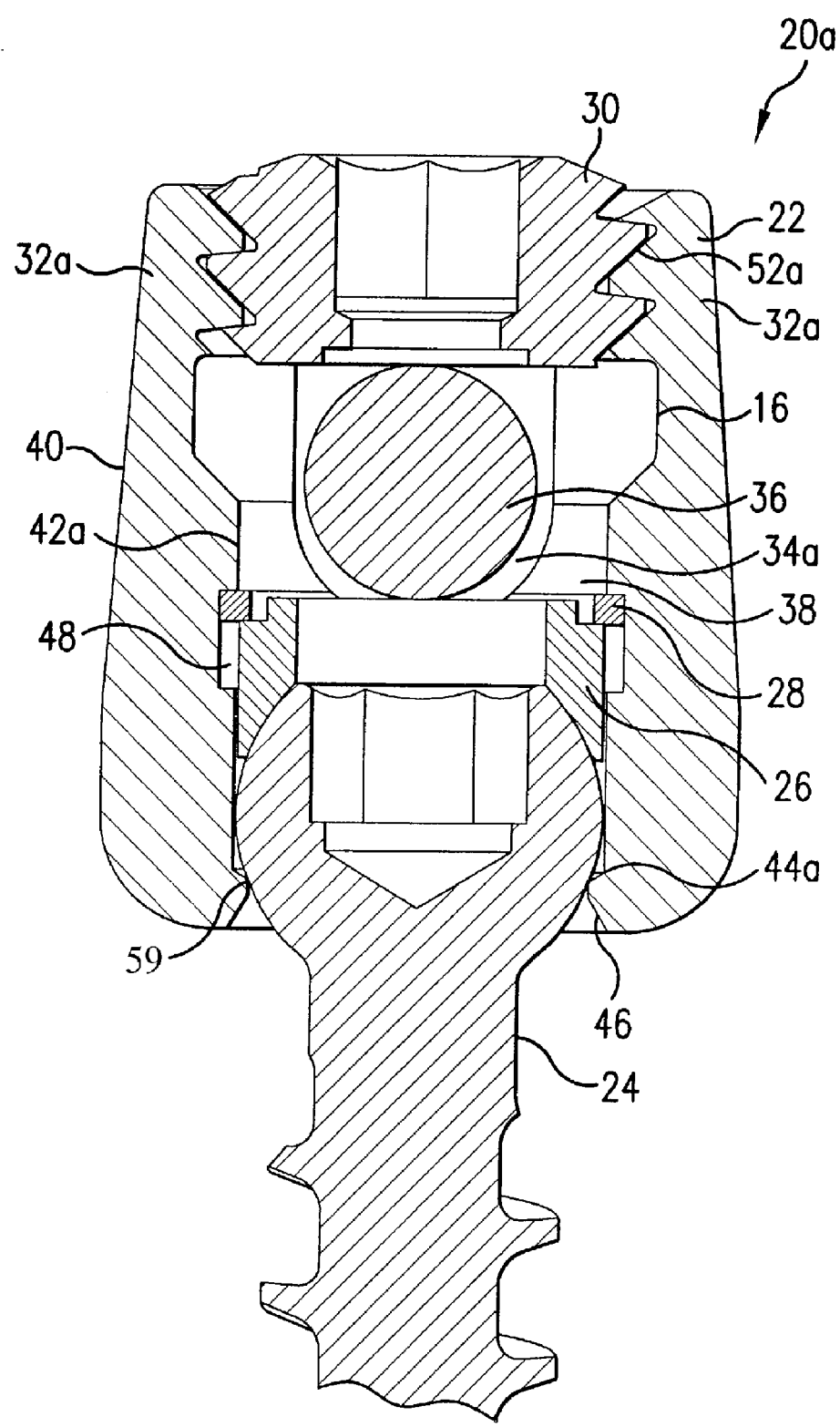
FIG. 2 shows a partial cross-sectional view of a bone anchor assembly according to another embodiment of the present invention.
Figure 19:
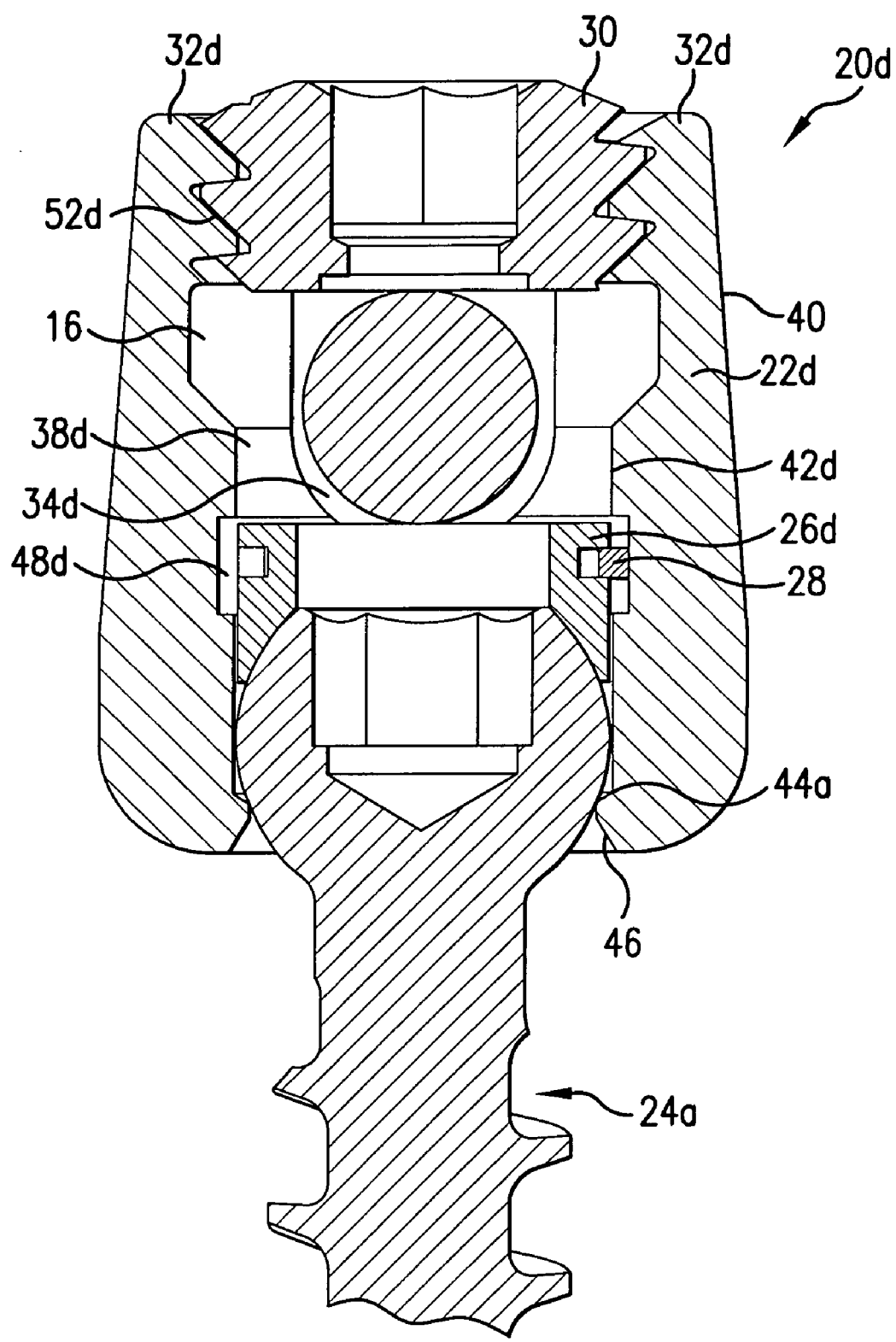
FIG. 19 shows a partial cross-sectional view of a bone anchor assembly according to another embodiment of the present invention.

In the particular embodiments of saddle member 22, illustrated in FIGS. 1, 2 and 19, upright portions 32 each have an outer surface 40 and an inner surface 42. Inner surfaces 42 are substantially parallel to the axis of hole 38, along a longitudinal axis of saddle member 22. In the embodiment shown in FIG. 3, outer surfaces 40 are angled with respect to inner surfaces 42 and the longitudinal axis of saddle member 22 with an inward taper, which taper allows for easier handling of the saddle member 22 and reduced bulk of saddle member 22. Near the bottom of saddle member 22, hole 38 is narrowed by a wall portion 44. In one embodiment the wall portion 44 contains a section 59 that is circular and the plane of which is substantially perpendicular to the longitudinal axis of hole 38. However wall portion 44 and section 59 may be of any shape as long as the diameter of hole 38 at section 59 of wall portion 44 is greater than that of shank 72 and less than that of head portion 58 of the of bone anchor member 24.

Figure 4:
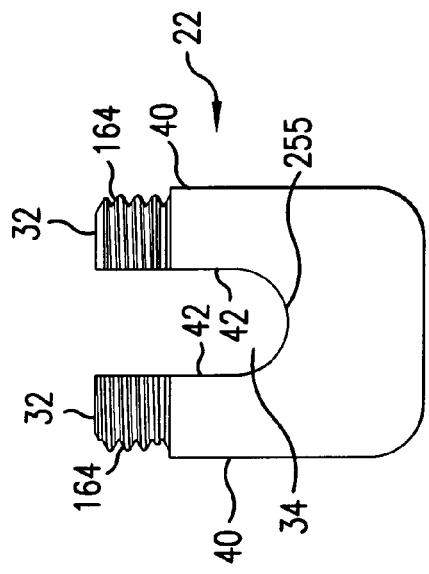
FIG. 4 shows a side view of a saddle member according to one embodiment of the present invention.

Upright portions 32 further include an internally threaded portion 52, as shown in FIG. 1. Internally threaded portion 52 is configured to be threadedly coupled with set screw 30, as described below. In other embodiments, as shown in FIGS. 2 and 19, the internally threaded portions 52a and 52d respectively are configured so that they end above rod 36 when set screw 30 is secured in saddle member 22. In one embodiment, as shown in FIGS. 2 and 19, saddle member 22 includes a relief groove 16 that extends around hole 38. Relief groove 16 eliminates the helical thread run out typically found on internal threads. In other embodiments, saddle member 22 does not contain a relief groove. In further embodiments, upright portions 32 may include an externally threaded portions 164, as shown in FIG. 4 instead of an internally threaded portions. Externally threaded portions 164 are configured to be threadedly coupled with external set screw 30a, as described hereafter. In this embodiment outer surfaces 40 are parallel to one another.

Below wall portion 44, hole 38 opens outward by virtue of a conical wall portion 46. Conical wall portion 46 allows bone anchor member 24 to be positioned in any of an infinite number of limited angular positions relative to the longitudinal axis of the saddle member 22 by reducing interference of the lower portion of saddle member 22 with a shank portion 72 of bone anchor member 24.

As shown in FIGS. 23-27, wall portion 44 conical wall portion 46 contain angular cutouts 62 placed symmetrically about the longitudinal axis of hole 38 to increase the allowable angulation of the bone screw in relation to the longitudinal axis of hole 38. Any number of cutouts, the shape of the cutouts, the position of the cutouts in relation to the axis of channel 34, the angle of the cutouts in relation to a plane that is perpendicular to the axis of hole 38, the size of the cutouts and the angular spacing between each cutout may vary for specific applications. As shown in the embodiment in FIGS. 23 and 24, there are three angular cutouts that are generally cylindrical in shape. Two of angular cutouts 62 being offset 30 degrees from the axis of channel 34 and all three angular cutouts 62 are spaced 120 degrees apart from one another. As shown in the embodiment in FIGS. 25 and 26, there are three angular cutouts that are generally cylindrical in shape. One of angular cutouts 62 being on the axis of channel 34 and all three angular cutouts 62 are spaced 120 degrees apart from one another.

Figure 8:
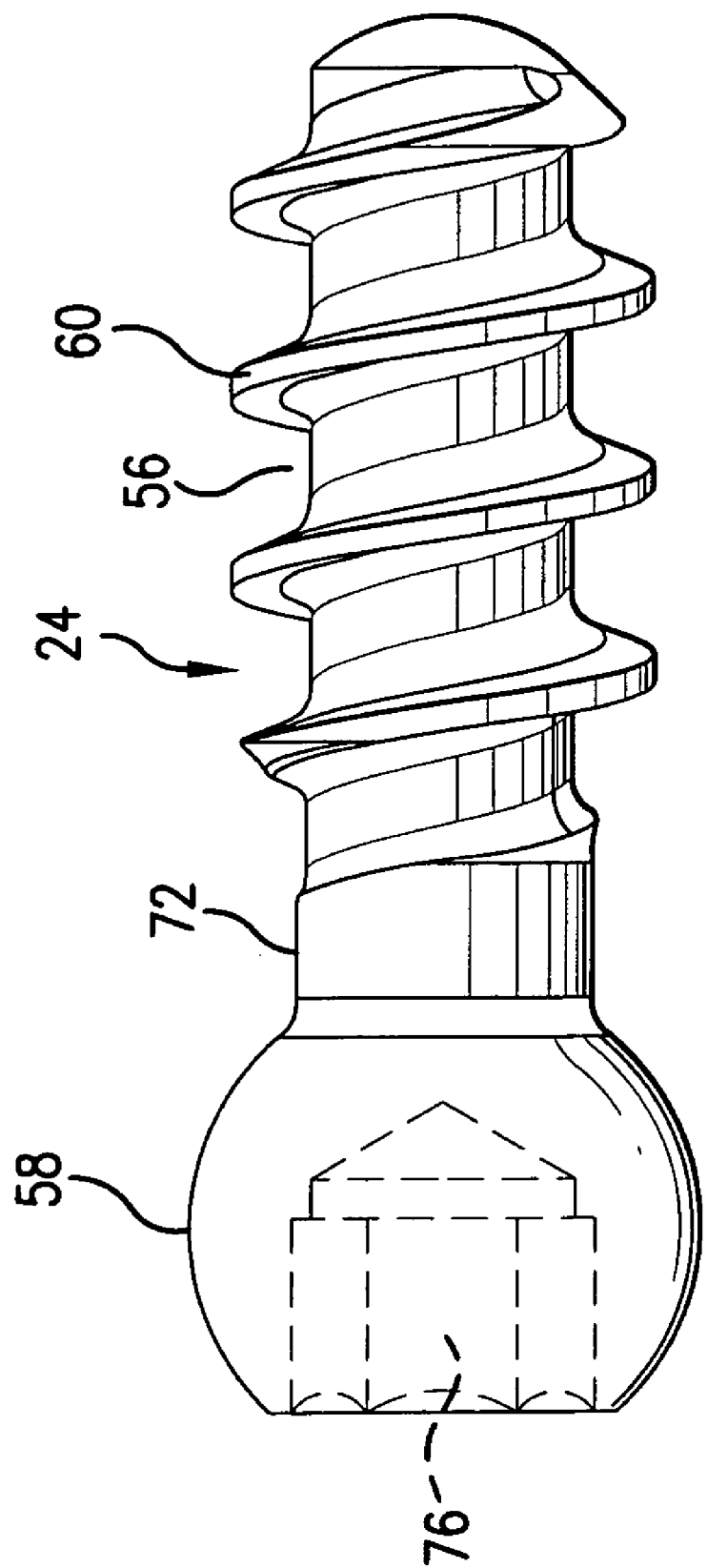
FIG. 8 shows a side view of an anchor member according to one embodiment.

As shown in FIG. 8, one embodiment of the bone anchor member 24 of the present invention has a threaded portion 56 containing threads 60, a shank 72 and a head portion 58. Head portion 58 of bone anchor member 24 in one embodiment is substantially spherical. However it should be understood that any external contour which is equidistant from the center point of the head portion 58 could be utilized. In the illustrated embodiment, a tool-engaging recess 76 is formed in the upper portion of head portion 58. The specific shape of tool-engaging recess 76 may be chosen to cooperate with any suitable screw-driving tool. In relation to each other, the diameter of the threaded portion 56 should be less than the diameter of the head portion 58, and the shank 72 should be narrower than the widest portion of threaded portion 56. As is apparent, any head design, shaft design, thread pitch or tip taper suitable for insertion into a vertebral body can be utilized. Threaded portion 56 can even be larger than head portion 58 if the thread pitch allows threading through wall portion 44.

Multi-axial bone anchor assembly 20 may further include a set screw 30. In the embodiments, illustrated in FIGS. 13-14, set screw 30 is generally cylindrical and has external threads 102. External threads 102, in one embodiment, are buttress threads. In another embodiment, threads 102 could be reverse angle threads so as to minimize splaying between the two upright members 32. An example of such reverse angle threading is disclosed in U.S. Pat. No. 6,296,642, which is hereby incorporated by reference.

Figure 14:
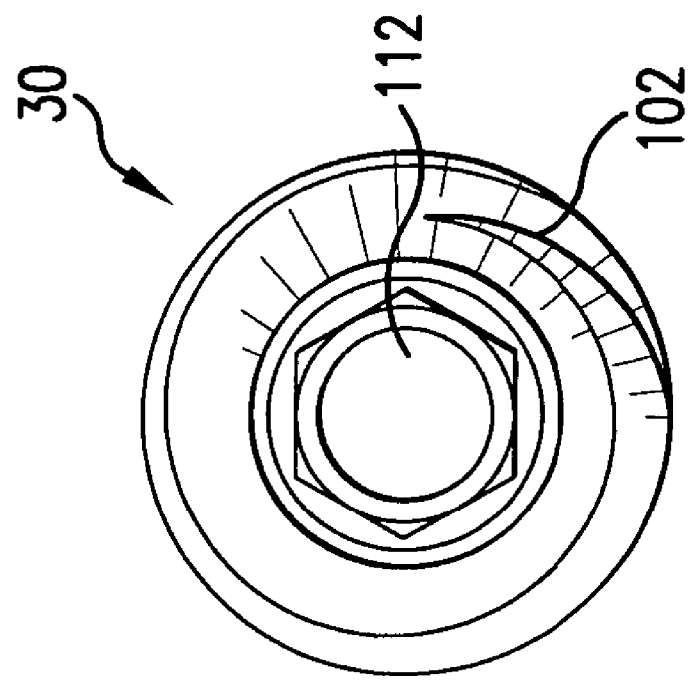
FIG. 14 shows a top view of the set screw of FIG. 13.
Figure 13:
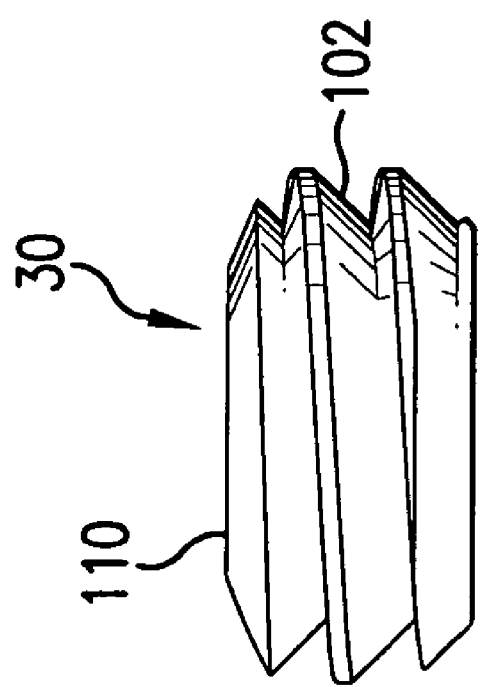
FIG. 13 shows a side view of a set screw according to one embodiment of the present invention.

As illustrated in FIGS. 13-14, this embodiment of set screw 30 includes a substantially flat end surface 110 in order to minimize the profile of assembly 20. Set screw 30 further includes a tool-engaging bore 112. Tool-engaging bore 112 is used in conjunction with a tool for introducing set screw 30 into saddle member 22.

Figure 16:
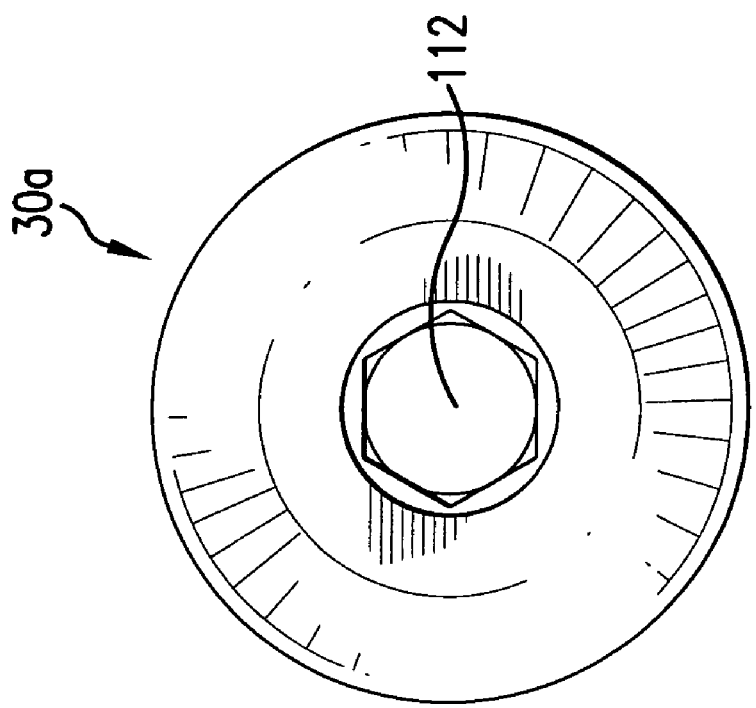
FIG. 16 shows a top view of the external set screw of FIG. 15.
Figure 15:
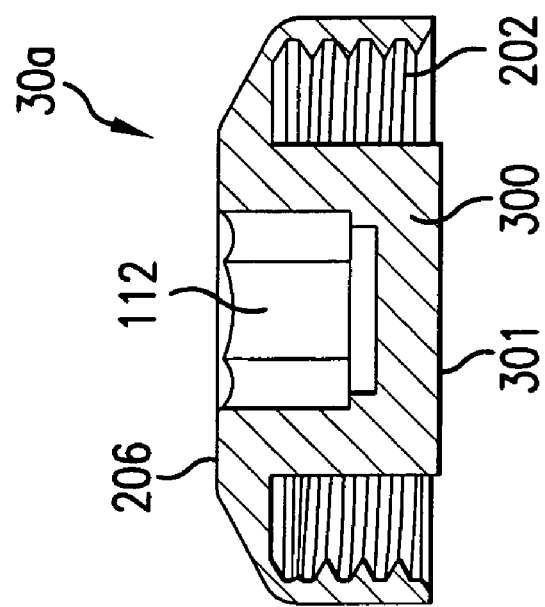
FIG. 15 shows a cross-sectional view of an external set screw according to another embodiment of the present invention.

In another embodiment, as illustrated in FIGS. 15-16, set screw 30a comprises internal threading 202 which is intended to mate with external threading 164 on the upwardly extending members 32 of saddle member 22. The set screw also comprises an inner plug portion 300 having a bottom surface which is intended to seat against the top surface of rod 36 seated in saddle 22, providing a means for driving the rod 36 downward against the head portion of bone anchor member 24 in one embodiment and against the washer 26 in another embodiment. In another embodiment, the bottom surface 301 of inner plug 300 comprises a plurality of raised metal projections to engage and press into rod 36. Set screw 30a has at one end a tool-engaging bore 112. As illustrated in FIG. 15, set screw 30a may also include a rounded end surface 206 to reduce internal trauma to a patient or a substantially flat end surface in order to minimize the profile of assembly 20. Tool-engaging bore 112 is used in conjunction with a tool for introducing set screw 30a onto saddle member 22.

In FIG. 2, there is shown a multi-axial bone anchor assembly 20a according to another embodiment of the present invention. Similar to the embodiment in FIG. 1 and described above, bone anchor assembly 20a includes a bone anchoring member 24 and a set screw member 30. However, this embodiment also comprises a washer (crown member) 26. Also in this embodiment, the internally threaded portions 52a are configured so that they end above rod 36 when set screw 30 is secured in saddle member 22. Saddle member 22 further includes a relief groove 16 that extends around hole 38. In some embodiments, assembly 20a will further include a C-shaped snap ring 28, which are fitted with saddle member 22 as will be described hereafter.

Figure 5:
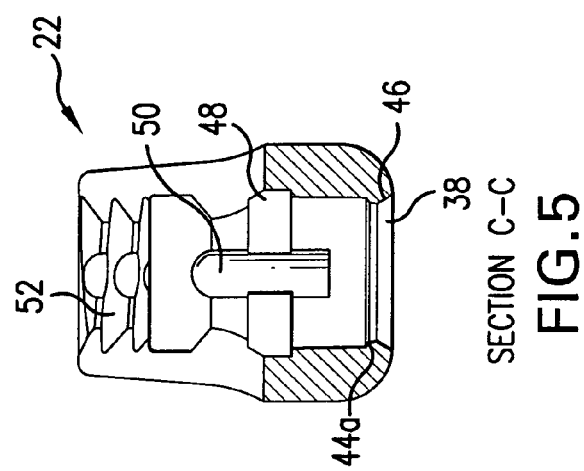
FIG. 5 shows a cross-sectional view of the saddle member according to one embodiment of the present invention.
Figure 7:
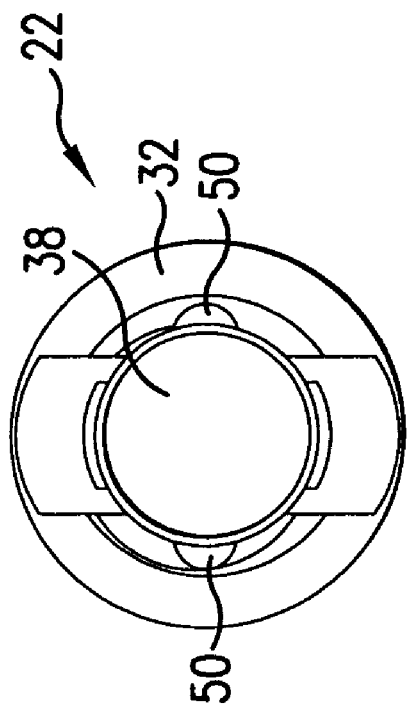
FIG. 7 shows a top view of the saddle member of FIG. 2.
Figure 6:
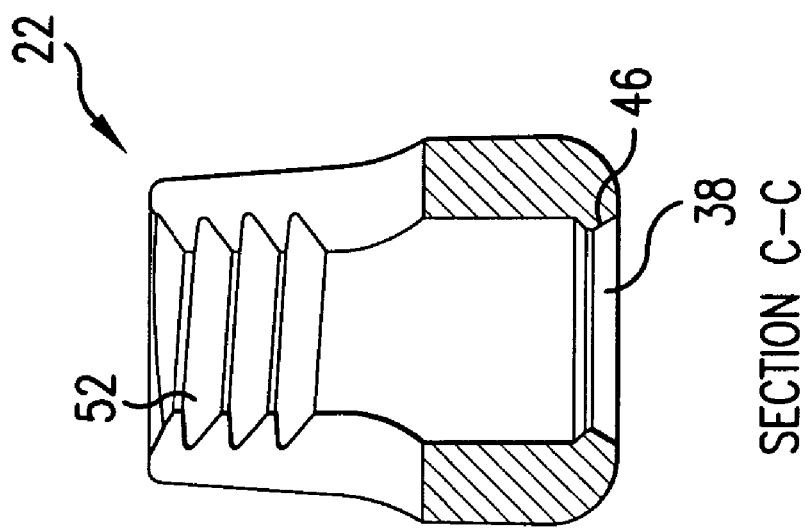
FIG. 6 shows a cross-sectional view of the saddle member according to another embodiment of the present invention.

The illustrated embodiment of FIGS. 2, 5 and 7 also comprises a saddle member 22 that further includes an inner groove 48 that extends around hole 38. Groove 48 is configured to accommodate snap ring 28 in a compressed condition, i.e., the outer diameter of groove 48 is at least slightly smaller than the normal uncompressed outer diameter of snap ring 28. The illustrated embodiment of saddle assembly 22 further includes one or more troughs 50 extending longitudinally within each of upright portions 32. The one or more troughs 50 accommodates placement of washer 26, as further described below, and may have a rounded (e.g. cylindrical), squared, or other appropriate shape to accommodate washer 26. In this embodiment, the curved bottoms 255 of channel 34 are arranged such that when rod 36 is inserted therein, rod 36 will pressingly engage the washer 26 which will itself pressingly engage the head portion 58 of bone anchor member 24.

Referring now to FIGS. 9-12, there is shown an embodiment of washer 26 of the present invention. Washer 26 includes an upper portion 80, a lower portion 82, and a hole 84 therethrough. Upper portion 80 and lower portion 82 may be constructed integrally or may be separately constructed and attached together in any known manner. An upper surface 86 of upper portion 80 may include recessed portions 88 in the illustrated embodiment, which recessed portions 88 form a part of a cylinder sized and configured to accommodate placement of an elongated member (such as rod 36 of FIG. 1) therein. Lower portion 82 further includes an upper surface 83 that faces snap ring 28.

Figure 11:
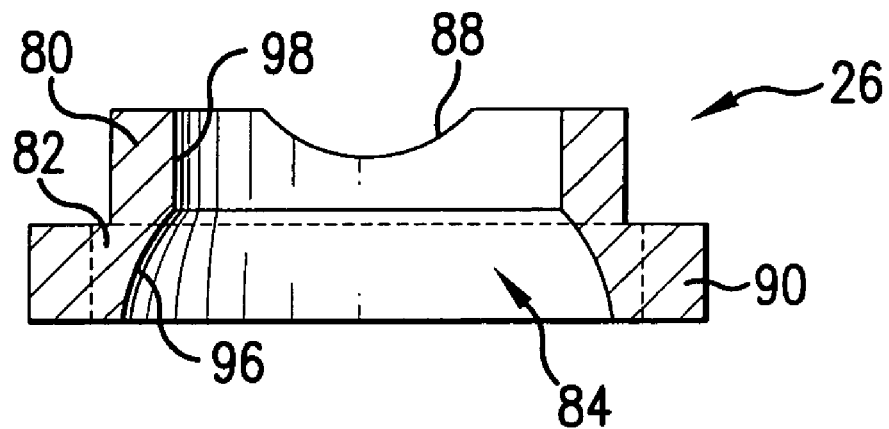
FIG. 11 shows a cross-sectional view of the washer of FIG. 9
Figure 12:
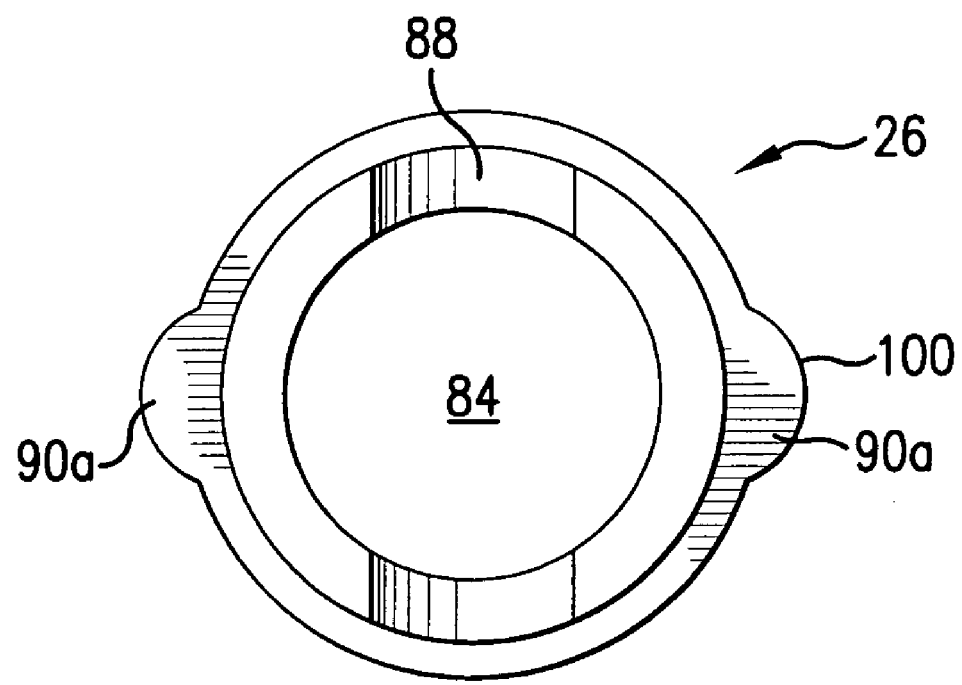
FIG. 12 shows a top view of another embodiment of a washer according to the present invention.

Referring now to FIG. 11, washer 26 has a hole 84 provided through both upper portion 80 and lower portion 82. Hole 84 includes a lower concave surface 96 and a cylindrical surface 98. Concave surface 96 in one specific embodiment has a spherical shape so as to substantially coincide with a portion of head portion 58 of anchoring member 24. Lower portion 82 is generally in the shape of a circular disc, and may include one or more projections 90 extending radially therefrom. Projections 90 in conjunction with troughs 50 align recessed portions 88 of washer 26 with channel 34a and prevent rotation of washer 26 so as to minimize misalignment between rod 36 and recessed portions 88.

Figure 9:
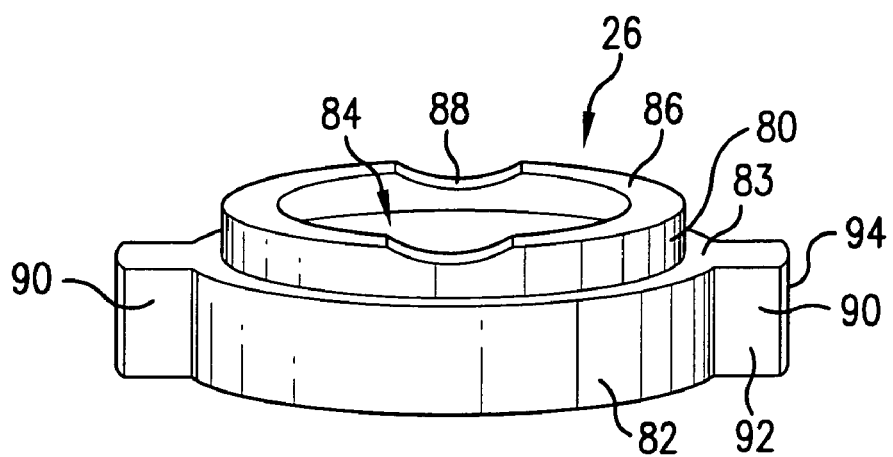
FIG. 9 shows a perspective view of a washer according to one embodiment of the present invention.
Figure 10:
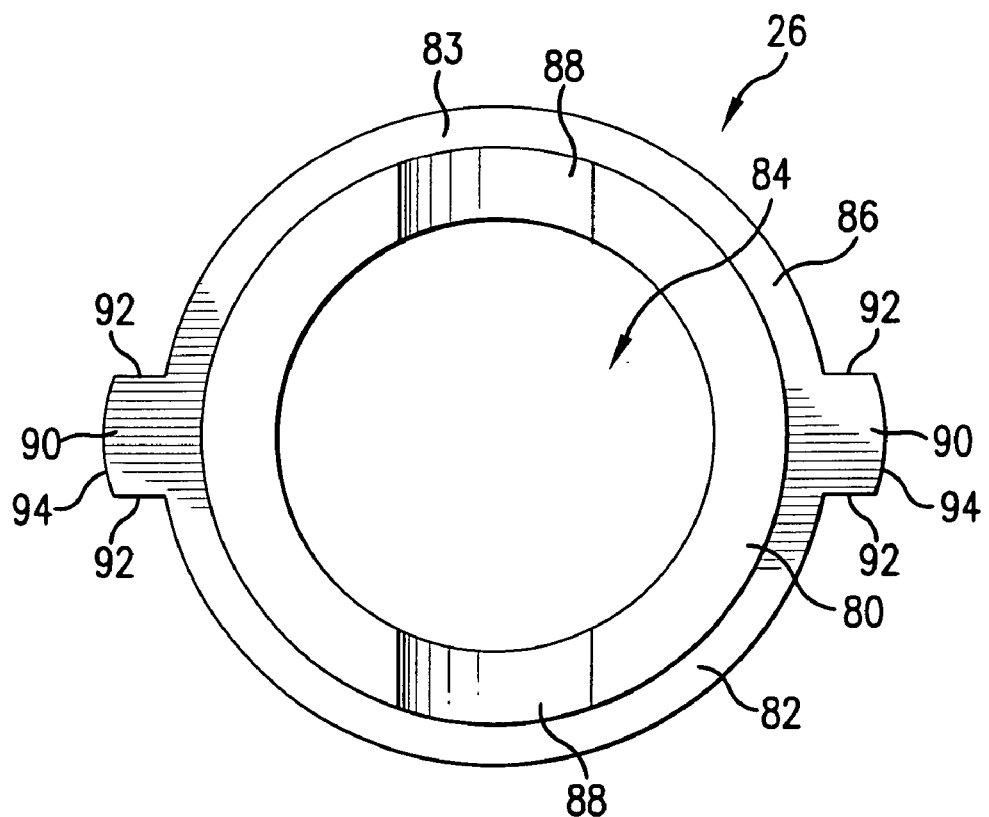
FIG. 10 shows a top view of the washer of FIG. 10.

In one embodiment, shown in FIGS. 9-10, projections 90 each include two substantially planar side surfaces 92, and an end surface 94 that is rounded and may form a portion of a cylinder. Projections 90 are sized and shaped so as to fit and slide easily within the troughs 50 upright portions 32a of saddle member 22. In another embodiment illustrated in FIG. 12, projections 90a each include a rounded end surface 100.

Figure 18:
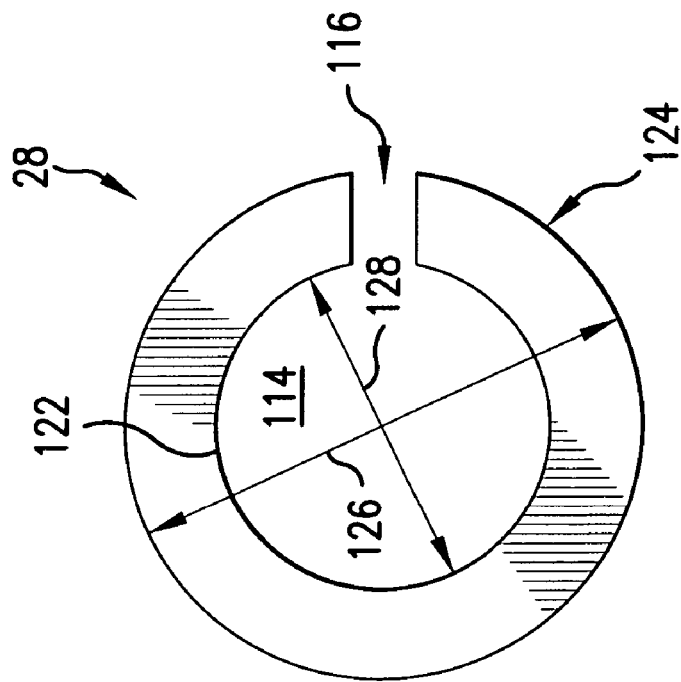
FIG. 18 shows a top view of the snap ring of FIG. 17.
Figure 17:
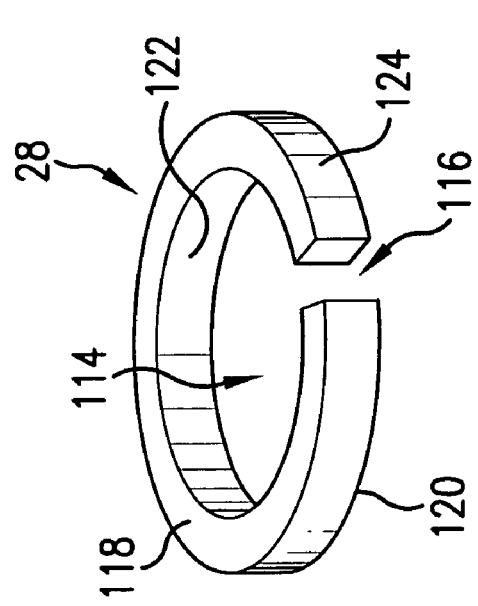
FIG. 17 shows a perspective view of a snap ring for use in the present invention.

In certain embodiments, multi-axial bone anchor assembly 20a includes snap ring 28 in order to secure washer 26 against anchoring member 24. One embodiment of such a snap ring 28 is shown in FIGS. 17-18. Snap ring 28 has a central opening 114 and a compression slot 116 defined therein. Snap ring 28 further has a first surface 118, an opposite second surface 120, an inner lateral surface 122 defining opening 114, and an outer lateral surface 124. Compression slot 116 allows snap ring 28 to compress and fit into inner groove 48 of saddle member 22. The diameter of the entrance of groove 48 is at least slightly smaller than the outer diameter 126 of an uncompressed snap ring 28. Opening 114 of snap ring 28 has an inner diameter 128, which allows snap ring 28 to fit around upper portion 80 of washer 26. One of the surfaces 118 and 120 engage the upper surface 83 of lower portion 82 in order to secure washer 26. Snap ring 28 can have a square cross-section, as shown in FIG. 2, or a circular or other appropriate shape cross-section, and in one particular embodiment is made of a shape memory alloy such as nitinol.

Figure 17A:
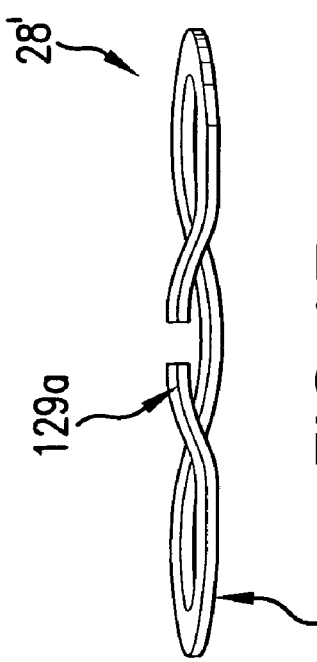
FIG. 17a shows a side view of an alternative embodiment of a snap ring for use in the present invention.

Another embodiment of snap ring 28' is illustrated in FIG. 17a. Snap ring 28' is non-planar, and in one embodiment has a series of undulations forming relative crests 129a and relative troughs 129b therein. Alternatively, non-planar snap ring 28' could have other curved configurations, or could have extending finger-spring elements along it. When assembly 20a is assembled, non-planar snap ring 28' allows less play between saddle member 22, anchoring member 24 and washer 26 because non-planar snap-ring 28' fills a greater portion of groove 48 of saddle member 22.

In FIG. 19, there is shown another embodiment of a multi-axial bone anchor assembly 20d according to another embodiment of the present invention. Similar to the embodiment in FIG. 1 and described above, bone anchor assembly 20d includes a bone anchoring member 24 and a set screw member 30. However, this embodiment also comprises a washer (crown member) 26d. In some embodiments, assembly 20d will further include a C-shaped snap ring 28, which are fitted with saddle member 22d as will be described hereafter.

Figure 20:
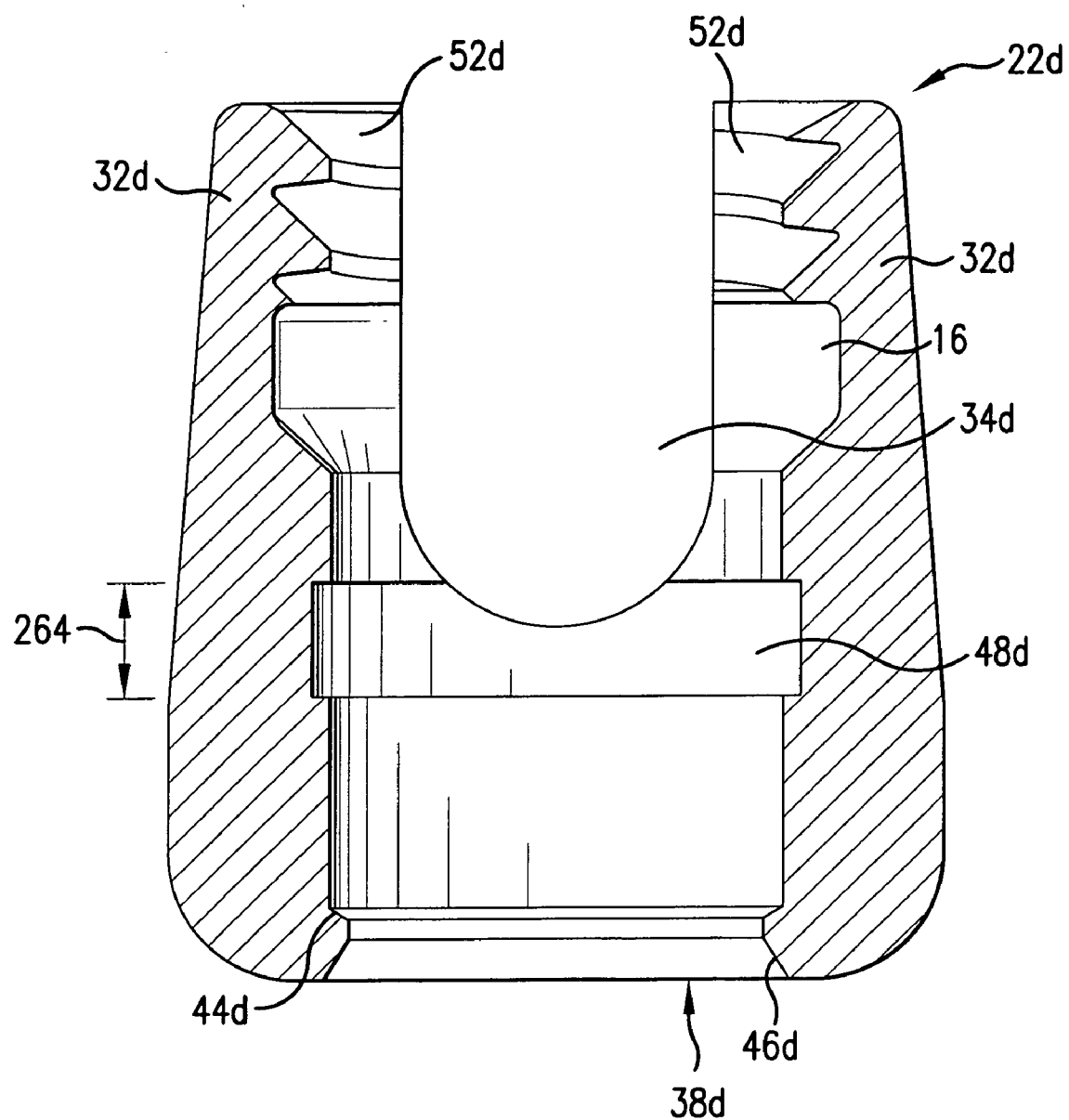
FIG. 20 shows a cross-sectional view of an embodiment of a saddle member shown in FIG. 19.
Figure 21:
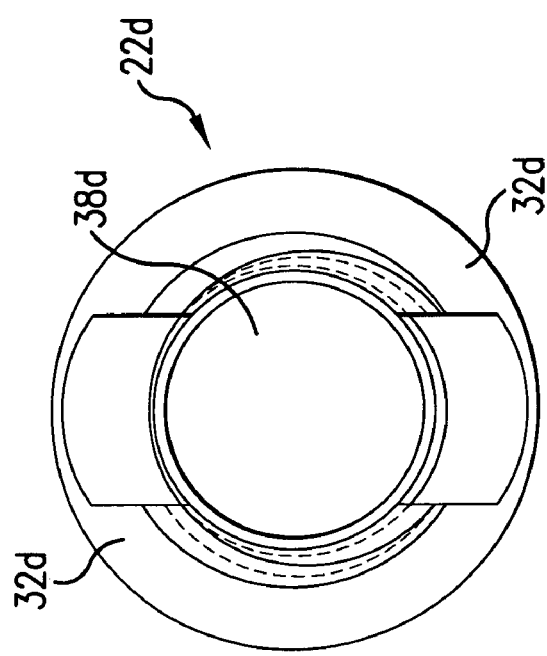
FIG. 21 shows a top view of the saddle member of FIG. 20.
Figure 23:
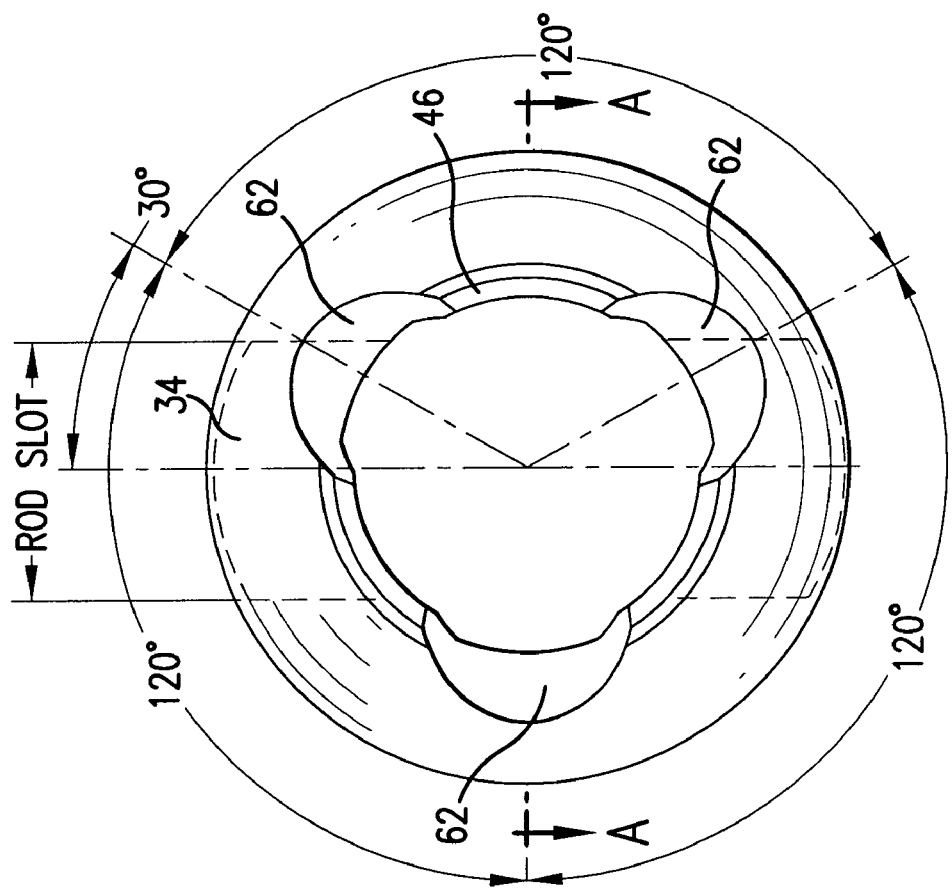
FIG. 23 shows a bottom view of the saddle member according to one embodiment of the present invention.
Figure 24:
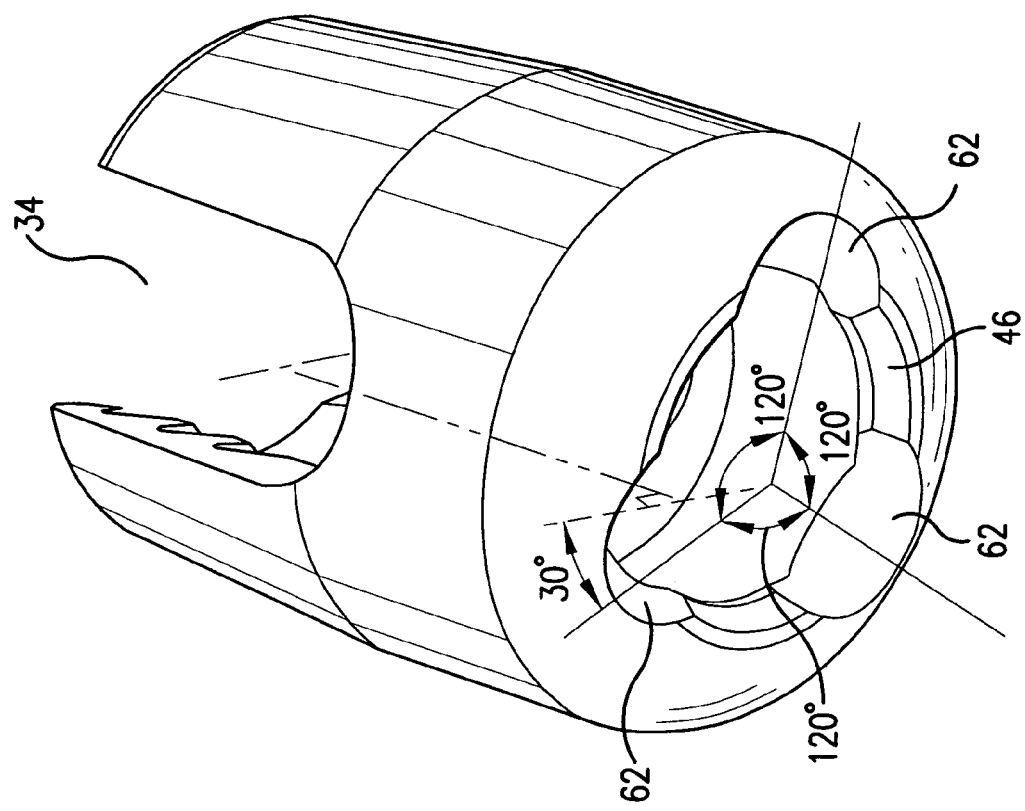
FIG. 24 shows an isometric view of a saddle member of FIG. 23.
Figure 25:
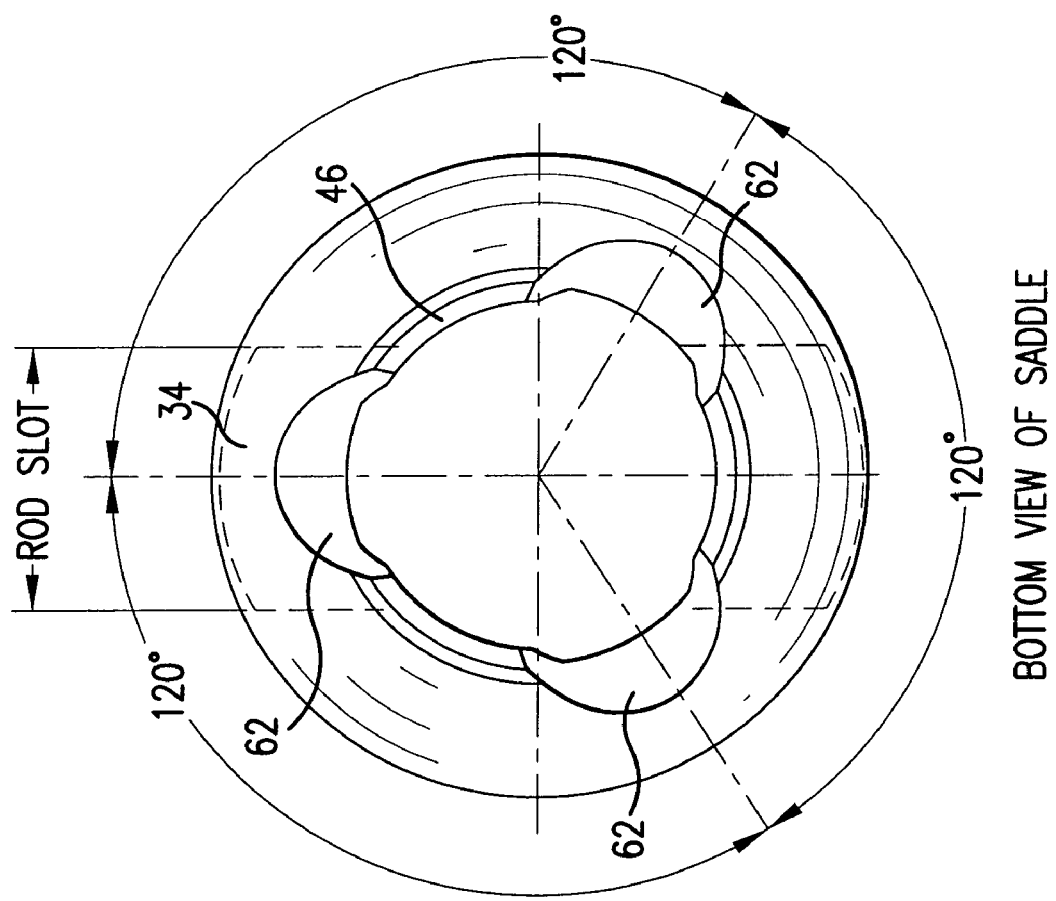
FIG. 25 shows a bottom view of the saddle member according to one embodiment of the present invention.
Figure 26:
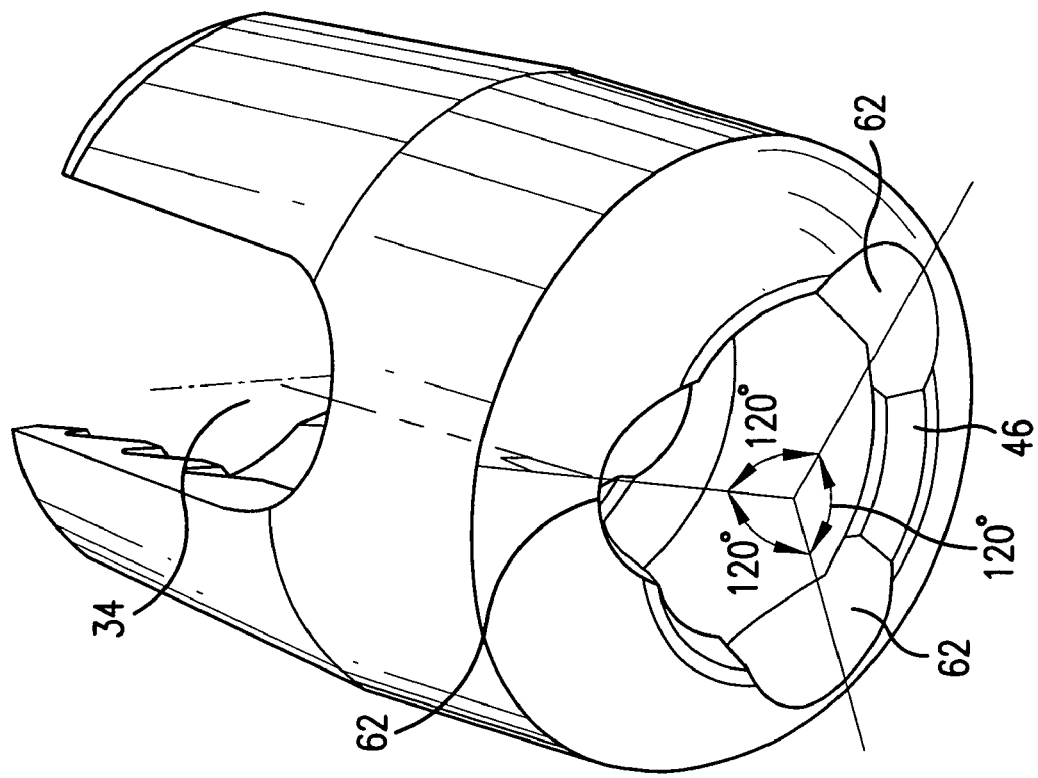
FIG. 26 shows an isometric view of a saddle member of FIG. 25.
Figure 27:
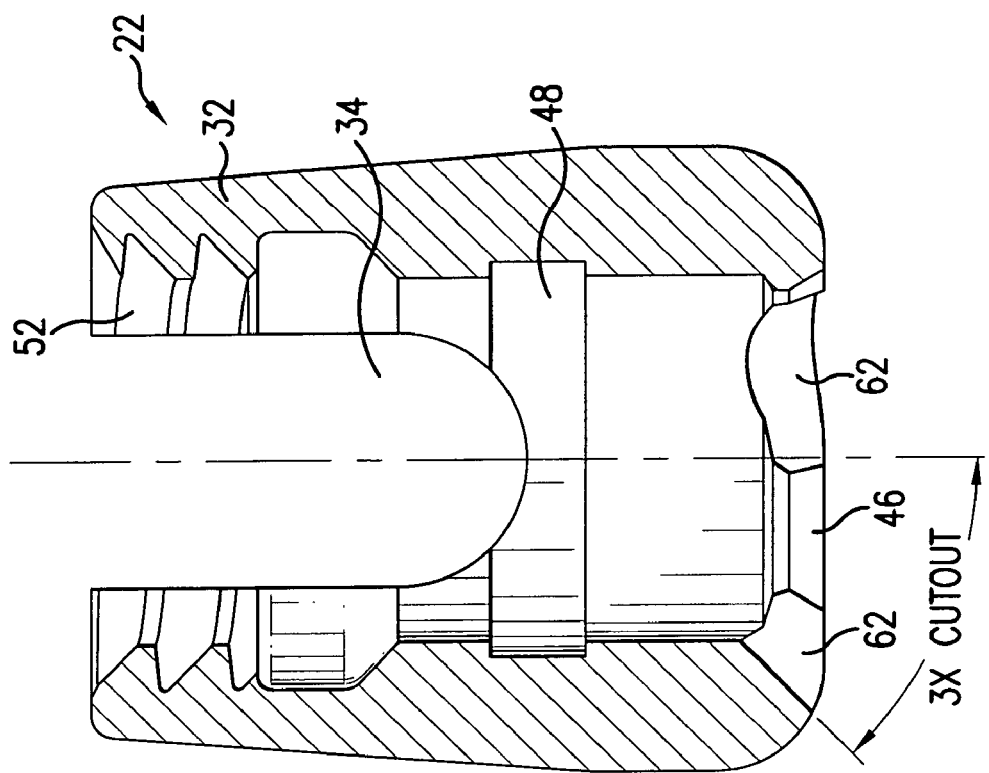
FIG. 27 shows a cross-sectional view of the saddle member according to one embodiment of the present invention.

The particular illustrated embodiment of saddle member 22d may include an inner groove 48d. As illustrated, groove 48d extends around hole 38d, and in this particular embodiment, groove 48d is uniform between a top portion of groove 48d and the bottom portion thereof. Groove 48d is configured to accommodate snap ring 28 in a compressed condition. Groove 48d has a thickness 264 that is, in one form, larger than snap ring 28. Further, the illustrated embodiment of saddle assembly 22d in FIGS. 20-21 does not include a trough 50 that extends longitudinally within each of upright portions 32d. Upright portions 32d further include internally threaded portions 52d, which are configured to be threadedly coupled with set screw 30.

Figure 22:
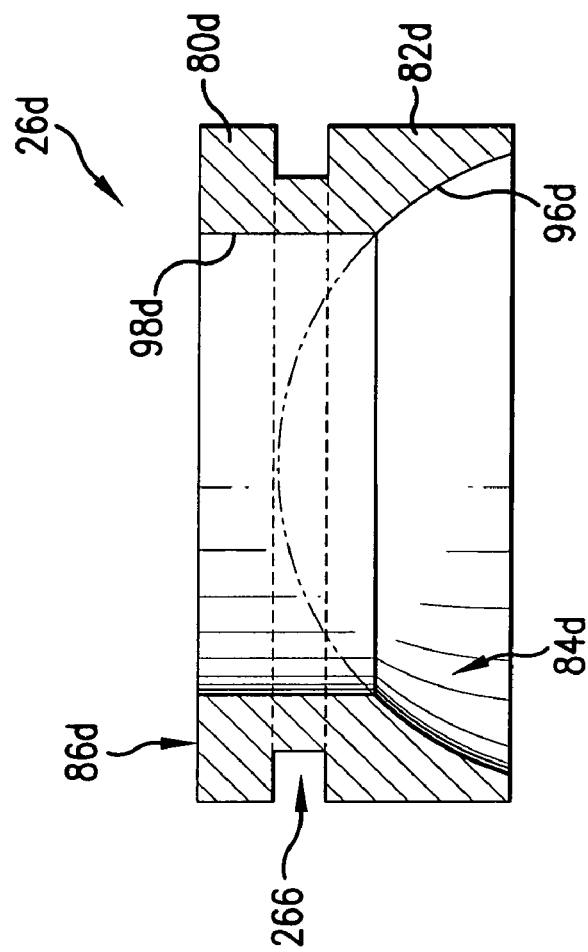
FIG. 22 shows a cross-sectional view of a washer shown in FIG. 19.

Referring now to FIG. 22, there is shown another embodiment of washer 26d according to the present invention. Washer 26d includes an upper portion 80d, a lower portion 82d, a snap ring recess 266, and a hole 84d therethrough. Upper portion 80d, lower portion 82d, and snap ring recess 266 may be constructed integrally or may be separately constructed and attached together in any known manner. Snap ring 28 fits within recess 266 in order to secure washer 26d within saddle member 22d. In one embodiment, assembly 20d is assembled by inserting anchoring member 24a through hole 38d in saddle member 22d. Washer 26d, with snap ring 28 in at least a portion of recess 266, is then inserted into hole 38d. Snap ring 28 contracts into recess 266 as washer 26d goes through saddle member 22d, and expands into groove 48d to hold washer 26d within saddle member 22d. An elongated member is then inserted in channel 34d, and a set screw (such as those described above) is threaded into internally threaded portions 52d, saddle member 22d to lock the elongated member, washer 26d and anchoring member 24a together.

Washer 26d has a hole 84d provided through both upper portion 80d and lower portion 82d. Hole 84d includes a lower concave surface 96d and a cylindrical surface 98d. Lower concave surface 96d opposite from upper surface 86d is adapted to accommodate head portion 58a of anchor member 24a. In the particular embodiment illustrated in FIG. 22, lower portion 82d is generally in the shape of a circular disc. In this particular embodiment, lower portion 82d does not have projections 90.

While embodiments of the invention have been illustrated and described in detail in the drawings and foregoing description, the same is to be considered as illustrative and not restrictive in character. It should be understood that only the preferred embodiments have been shown and described.

What is claimed is:

1. A multi-axial bone attachment assembly, comprising:
   a bone anchoring member comprising a head portion and an anchoring portion;
   a saddle member having a plurality of upright portions that define a channel through said saddle member such that an elongated rod may be received therein, wherein said upright portions include threaded portions, said saddle member further having a hole therethrough bounded by an inner wall through which said bone anchoring member may be inserted, said hole forming a lower opening in said saddle member that engages the head of the bone anchoring member such that the head of the bone anchoring member is prevented from passing therethrough, wherein said lower opening contains a plurality of angular cutouts placed symmetrically about the longitudinal axis the saddle member, the plurality of angular cutouts sized to receive a portion of the bone anchoring member to increase an allowable angulation of the bone anchoring member in relation to a longitudinal axis of the hole; and
   a set screw for threadedly engaging the threaded portions of the plurality of upright portions, said set screw further comprising an engaging portion for engaging the elongated rod.

2. The assembly of claim 1, wherein said upright portions are internally threaded, and said set screw is externally threaded.

3. The assembly of claim 2, wherein said threaded portions have reverse angle threads.

4. The assembly of claim 1, wherein said upright portions are externally threaded, and said set screw is internally threaded.

5. The assembly of claim 4, wherein said set screw includes an upper surface that is convexly rounded.

6. The assembly of claim 4, wherein said threaded portions have reverse angle threads.

7. The assembly of claim 1, wherein said anchoring member is a bone screw.

8. The assembly of claim 7, wherein said bone screw includes a head portion having a convex underside.

9. The assembly of claim 8, wherein said convex underside is spherical.

10. The assembly of claim 1, wherein the threaded portions are located above the elongated rod when the set screw is fully threadedly engaged within the plurality of upright portions.

11. The assembly of claim 10, wherein the inner wall includes a relief groove adjacent to the threaded portions.

12. The assembly of claim 1, further comprising a washer for accommodating the elongated rod, said washer being fitted within said hole of said saddle member and atop said bone anchoring member.

13. The assembly of claim 12, wherein the washer comprises a recessed portion for accommodating the elongated rod.

14. The assembly of claim 13, wherein said inner wall includes a groove, said assembly further comprises a snap-ring fitted into said groove to hold said washer in said hole of said saddle member.

15. The assembly of claim 13, wherein said upright portions each have one or more troughs defined therein, said washer includes one or more alignment members to mate therewith to minimize misalignment between the rod and said recessed portion.

16. The assembly of claim 15, wherein said upright portions are internally threaded, and said set screw is externally threaded.

17. The assembly of claim 15, wherein said upright portions are externally threaded, and said set screw is internally threaded.

18. The assembly of claim 12, wherein the threaded portions are located above the elongated rod when the set screw is fully threadedly engaged within the plurality of upright portions.

19. The assembly of claim 18, wherein the inner wall includes a relief groove adjacent to the threaded portions.

20. A multi-axial bone attachment assembly, comprising:
   a bone anchoring member comprising a head portion and an anchoring portion;
   a saddle member having a plurality of upright portions that define a channel through said saddle member such that an elongated rod may be received therein, wherein said upright portions include threaded portions, said saddle member further having a hole therethrough bounded by an inner wall through which said bone anchoring member may be inserted, said hole forming a lower circular opening in said saddle member that engages the head of the bone anchoring member such that the head of the bone anchoring member is prevented from passing therethrough, wherein said lower opening contains a plurality of angular cutouts placed symmetrically about the longitudinal axis the saddle member, the plurality of angular cutouts sized to receive a portion of the bone anchoring member to increase an allowable angulation of the bone anchoring member in relation to the longitudinal axis of the saddle member; and a set screw for threadedly engaging the threaded portions of the plurality of upright portions, said set screw further comprising an engaging portion for engaging the elongated rod.

21. The assembly of claim 20, wherein the circular opening is planar and substantially perpendicular to the longitudinal axis the saddle member.

22. The assembly of claim 20, wherein said upright portions are internally threaded, and said set screw is externally threaded.

23. The assembly of claim 22, wherein said threaded portions have reverse angle threads.

24. The assembly of claim 20, wherein said upright portions are externally threaded, and said set screw is internally threaded.

25. The assembly of claim 24, wherein said set screw includes an upper surface that is convexly rounded.

26. The assembly of claim 24, wherein said threaded portions have reverse angle threads.

27. The assembly of claim 20, wherein said anchoring member is a bone screw.

28. The assembly of claim 27, wherein said bone screw includes a head portion having a convex underside.

29. The assembly of claim 28, wherein said convex underside is spherical.

30. The assembly of claim 20, wherein the threaded portions are located above the elongated rod when the set screw is fully threadedly engaged within the plurality of upright portions.

31. The assembly of claim 30, wherein the inner wall includes a relief groove adjacent to the threaded portions.

32. The assembly of claim 20, further comprising a washer for accommodating the elongated rod, said washer being fitted within said hole of said saddle member and atop said bone anchoring member.

33. The assembly of claim 32, wherein the washer comprises a recessed portion for accommodating the elongated rod.

34. The assembly of claim 33, wherein said inner wall includes a groove, said assembly further comprises a snap-ring fitted into said groove to hold said washer in said hole of said saddle member.

35. The assembly of claim 34, wherein said upright portions each have one or more troughs defined therein, said washer includes one or more alignment members to mate therewith to minimize misalignment between the rod and said recessed portion.

36. The assembly of claim 35, wherein said upright portions are internally threaded, and said set screw is externally threaded.

37. The assembly of claim 35, wherein said upright portions are externally threaded, and said set screw is internally threaded.

38. The assembly of claim 32, wherein the threaded portions are located above the elongated rod when the set screw is fully threadedly engaged within the plurality of upright portions.

39. The assembly of claim 38, wherein the inner wall includes a relief groove adjacent to the threaded portions.

* * * * *